US012674804B2

(12) United States Patent
Kadnikov et al.

(10) Patent No.: US 12,674,804 B2
(45) Date of Patent: Jul. 7, 2026

(54) MODULAR CHEMICAL PROBE FOR DETECTION OF AMINO ACID CITRULLINE IN PHYSIOLOGICAL SAMPLES

(71) Applicant: WiSys Technology Foundation, Inc., Madison, WI (US)

(72) Inventors: Dmitry V. Kadnikov, Woodbury, MN (US); Jennifer E. Grant, Menomonie, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 862 days.

(21) Appl. No.: 17/628,808

(22) PCT Filed: Jul. 22, 2020

(86) PCT No.: PCT/US2020/043049

§ 371 (c)(1),
(2) Date: Jan. 20, 2022

(87) PCT Pub. No.: WO2021/016339

PCT Pub. Date: Jan. 28, 2021

(65) Prior Publication Data

US 2022/0276257 A1 Sep. 1, 2022

Related U.S. Application Data

(60) Provisional application No. 62/877,097, filed on Jul. 22, 2019.

(51) Int. Cl.
*G01N 33/68* (2006.01)
*C07C 47/277* (2006.01)
(Continued)

(52) U.S. Cl.
CPC ....... *G01N 33/6812* (2013.01); *C07C 47/277* (2013.01); *C07C 49/255* (2013.01);
(Continued)

(58) Field of Classification Search
None
See application file for complete search history.

(56) References Cited

U.S. PATENT DOCUMENTS

2014/0308676 A1 10/2014 Fert-Bober et al.
2015/0080245 A1 3/2015 Ju et al.
2016/0258961 A1 9/2016 Thompson et al.

OTHER PUBLICATIONS

Dacon, N. et al. "1,3-Dicarbonyl compounds as chemical probes for detection of amino acid citrulline" Abstracts, 53rd Midwest Regional Meeting of the American Chemical Society, Ames, IA, United States; Oct. 21-23, 2018 (Year: 2018).*

(Continued)

*Primary Examiner* — Medhanit W Bahta
(74) *Attorney, Agent, or Firm* — Boyle Fredrickson, S.C.

(57) ABSTRACT

An improved chemical probe for the detection of the amino acid citrulline combines: 1) a reactive head formed of 1,3-dicarbonyl moiety that reacts with a citrulline side chain in an improved manner compared to currently used 1,2-dicarbonyl moieties; and 2) a modular action of the probe where citrulline side chains are labeled first using reactive heads described above, and attachment of a read-out subunit or tag, be it a fluorophore, a nanoparticle, or an antigen is performed separately. The modular nature of the chemical probe increases the sensitivity of the probes due to their smaller size. Additionally, the chemical probes of the present disclosure allow the same sample to be analyzed using a variety of read-out methods.

20 Claims, 6 Drawing Sheets

(51) Int. Cl.
*C07C 49/255* (2006.01)
*C07C 49/258* (2006.01)
*C07C 49/755* (2006.01)
*C07C 49/757* (2006.01)
*G01N 33/533* (2006.01)
*G01N 33/543* (2006.01)

(52) U.S. Cl.
CPC .......... *C07C 49/258* (2013.01); *C07C 49/755* (2013.01); *C07C 49/757* (2013.01); *G01N 33/533* (2013.01); *G01N 33/54326* (2013.01); *G01N 33/6848* (2013.01)

(56) References Cited

OTHER PUBLICATIONS

Kadnikov, D. et al. "New reactive heads for detection of amino acid citrulline" Abstracts, 42nd Great Lakes Regional Meeting of the American Chemical Society, Fargo, ND, United States; Jun. 27-30, 2017 (Year: 2017).*

Ilyas, S. et al. "Selective Conjugation of Proteins by Mining Active Proteomes through Click-Functionalized Magnetic Nanoparticles" ACS Nano 2013, 7, 9655-9663 (Year: 2013).*

Lewallen et al., Chemical Proteomic Platform to Identify Citrullinated Proteins, ACS Chemical Biology, vol. 10, Sep. 11, 2015 [retrieved on Oct. 2, 2020]. Retrieved from the Internet: <URL: https://pubs.acs.org/doi/10.1021/acschembio.5b00438>. pp. 2520-2528.

Yem et al., Biotinylation of Reactive Amino Groups in Native Recombinant Human Interleukin-1β, The Journal of Biological Chemistry, vol. 264, No. 30, Oct. 25, 1989, pp. 17691-17697.

Samanta et al., A modified dinucleotide for site-specific RNA-labelling by transcription priming ans click chemistry, Chemical Communications, vol. 50, Oct. 17, 2013 [retried on Oct. 5, 2020]. Retrieved from the Internet: <URL: https://pubs.rsc.org/en/content/articlelanding/2014/CC/C3CC46132G#!divAbstract>. abstract and supplementary information pp. S1-S11.

* cited by examiner

4

5

6

7

MODULAR CHEMICAL PROBE FOR DETECTION OF AMINO ACID CITRULLINE IN PHYSIOLOGICAL SAMPLES

CROSS-REFERENCE TO RELATED APPLICATIONS

This application claims priority from U.S. Provisional Patent Application Ser. No. 62/877,097, filed on Jul. 22, 2019, the entirety of which is expressly incorporated herein by reference for all purposes.

FIELD OF THE INVENTION

The present invention relates generally to compounds for the detection of the presence of an amino acid citrulline in proteins from biological samples.

BACKGROUND OF THE INVENTION

The amino acid citrulline is produced via a post-translational modification of the side chain of amino acid arginine. This transformation leads to significant changes in the structure and function of proteins, which in turn often results in negative physiological changes. For example, citrullination is a post-translational modification of proteins that is the root cause of multiple sclerosis[1] and rheumatoid arthritis[1,2]; recently it has been correlated with chronic periodontitis.[3] Increasingly, evidence that citrullination may impact a variety of neurological disorders[1,4-6], cancer[1], and immunity in general[7] is being published. Despite the medical relevance of citrullination, however, there exist only a limited number of methods for identifying citrullinated proteins and the precise site of modification.

Rheumatoid arthritis affects more than 1.3 million Americans, and as much as 1% of the global adult population, and other autoimmune diseases afflict millions of people worldwide as well. Thus, efficient detection of citrulline would immediately provide a new research tool to investigate development of these diseases, and in future may create a clinical test for their detection.

Existing methods of detection of citrullination are either not selective (mass-spectrometry) or not sufficiently sensitive (anti-citrulline antibodies). The use of small molecules as chemical probes has thus emerged as a method of choice. However, the few chemical probes available right now are difficult to synthesize and cumbersome to use, which is reflected in their high prices (for example, $445/1 mg from Cayman Chemicals) and preclude wide adoption of the technology.

Despite the medical relevance of citrullination, however, there exist only a limited number of methods for identifying citrullinated proteins and the precise site of modification.

Mass-spectrometry has evolved into a powerful method of analysis of proteins and their component groups. However, this analysis method is not useful in this case because the difference in mass between arginine and citrulline is only 1 Dalton, and thus the selectivity of mass-spectrometry is not sufficient to provide an adequate distinction between the groups. In addition, detection is complicated since the difference can be mistaken for Carbon-13 isotope.

As an alternative, antibodies can detect the presence of citrulline, in method where detection of citrullinated protein is performed by the derivatization of citrulline with phenylglyoxal, which generates a cyclic moiety that could be recognized by anti-citrulline antibodies. However, these antibodies are able to determine the presence of citrulline only in large concentrations which omits a large portion of positive test results that would be highly useful in autoimmune diagnoses, such that these detection methods do not have sufficient sensitivity to be practical.

More recently, chemical probes have emerged as a method of choice for citrulline detection. Chemical probes are small organic molecules, which contain 1) a reactive head that selectively reacts with a biological molecule of interest; and 2) a moiety that allows detection of this reaction product.

While able to provide accurate detection of citrulline, a main shortcoming of the few chemical probes available right now is that they are difficult to synthesize and cumbersome to use, which is reflected in their high prices, all of which preclude widespread adoption of the technology.

Therefore, it is desirable to develop new chemical probes that overcome the deficiencies of the prior art.

SUMMARY OF THE INVENTION

Briefly described, according to an exemplary embodiment an improved chemical probe for the detection of the amino acid citrulline combines: 1) a reactive head formed of 1,3-dicarbonyl moiety that reacts with a citrulline side chain in an improved manner compared to currently used 1,2-dicarbonyl moieties; and 2) a modular action of the probe where citrulline side chains are labeled first using reactive heads described above, and attachment of a read-out subunit, be it a fluorophore, a nanoparticle, or an antigen is performed separately. The modular nature of the chemical probe increases the sensitivity of the probes due to their smaller size. Additionally, the chemical probes of the present disclosure allow the same sample to be analyzed using a variety of read-out methods.

Model systems containing different 1,3-dicarbonyl moieties have been synthesized and shown to react with N-ethylurea, a model compound mimicking the urea functional group of a citrulline side chain.

Several read-out tags have also been synthesized and shown that they are effective in a click reaction that will be used to attach the read-out subunit to a labeled citrulline molecule.

Numerous other aspects, features, and advantages of the invention will be made apparent from the following detailed description.

BRIEF DESCRIPTION OF THE DRAWING FIGURES

The drawing figures illustrate the best mode currently contemplated of practicing the present invention.

DETAILED DESCRIPTION OF THE INVENTION

Figure 1:
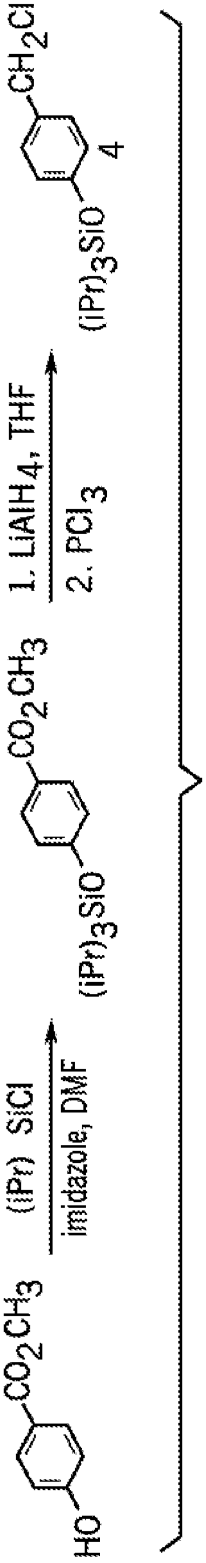
FIG. 1 is a scheme for the synthesis of a protected p-hydroxybenzyl chloride according to the present disclosure.

Reference will now be made in detail to various embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Experimental Section

A.) Synthesis of a Ketoaldehyde Reactive Head Bearing an Alkyne Moiety for Attachment of a Read-out Subunit Several model reactive heads shown below have been successfully synthesized and examined for their reactivity with a model compound, N-ethylurea, which accurately simulates the reactivity of citrulline.

The general structure of the reactive heads that were initially developed included a 1,3-dicarbonyl substructure shown below which can come in three varieties, from left to right, ketone-ketone, ketone-aldehyde, and aldehyde-aldehyde.

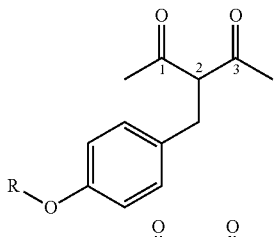

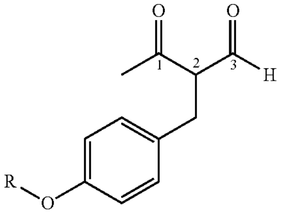

-continued

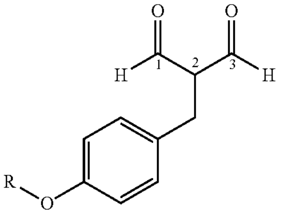

Initial efforts were focused on the model probe compounds where R═$CH_3$, though R can be any suitable reactive head linker that can be attached to the detection tag and/or the probe linker forming a part of the detection tag along with the read-out tag, including but not limited to an alkyne, an alkene, an alkyl, or a nitrogen, sulfur, phosphorous or oxygen-containing functional group, such as a C═O-alkyl group or (C═O)—O-alkyl group, and a PEG-based linker —$(OCH_2CH_2)_n$, where n=2 to 12, among others.

The ketone-ketone (1) and ketone-aldehyde (2) compounds were synthesized directly, but for the aldehyde-aldehyde we synthesized a modified compound 3 with an additional $CH_3$ attached to the carbon at position 2. This aldehyde-aldehyde reactive head compound has the functionality to react with the urea functional group of the citrulline which has also been demonstrated using ketone-ketone and ketone-aldehyde reactive head compounds.

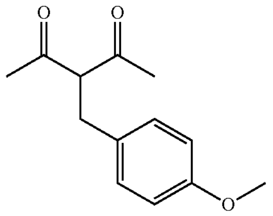

1

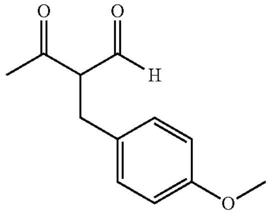

2

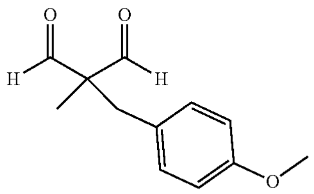

3

The following are the exemplary synthesis schemes for reactive tag or head structures 1, 2 and 3, and reactions of the reactive heads 1 and 2 with N-ethylurea demonstrating their capability of attaching to a citrulline molecule via a reaction with the urea functional group in its side chain.

I. Model Reactive Heads

3-(4-Methoxybenzyl)pentane-2,4-dione (1)

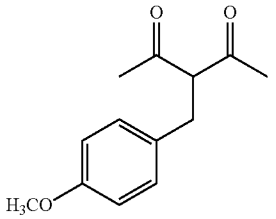

1

Synthesis sequence

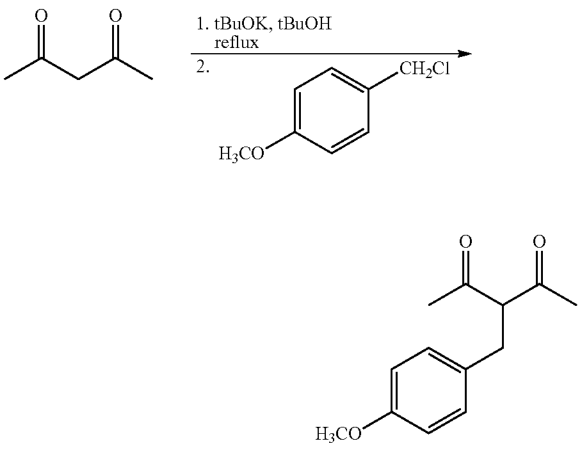

Procedures for Scheme

Potassium Cert-butoxide (2.24 g, 20 mmol) was dissolved in tert-butyl alcohol (20 mL) by refluxing for 25 min. The reaction mixture was cooled to room temperature and 2,4-pentanedione (2.11 g, 21 mmol) was added dropwise over 20 min, followed by 4-methoxybenzyl chloride (2.41 g, 19 mmol). The reaction mixture was left to stir at room temperature overnight. Water (40 mL) was added and the resulting mixture was extracted with ethyl acetate. Organic extracts were combined, dried over anhydrous magnesium sulfate, and concentrated under reduced pressure. The crude product was purified via column chromatography on silica gel to afford the desired product 1 as a white solid (2.37 g, 57%).

The product was obtained as a 3:1 mixture of enol and ketone tautomer which is reflected in its NMR data: $^1H$ NMR ($CDCl_3$, 300 MHz) δ enol tautomer (major): 7.07 (d, J=8.4 Hz, 2H), 6.87 (d, J=8.4 Hz, 2H), 3.81 (s, 3H), 3.61 (s, 2H), 2.09 (s, 6H): ketone tautomer (minor): 7.09 (d, J=8.1 Hz, 2H), 6.82 (d, J=8.7 Hz, 2H), 3.98 (t, J=7.7 Hz, 1H), 3.79 (s, 3H), 3.11 (d, J=7.5 Hz, 2H), 2.14 (s, 6H); $^{13}C$ NMR ($CDCl_3$, 75 MHz) δ enol tautomer (major): 191.9, 158.1, 131.6, 128.3, 114.06, 108.6, 55.3, 32.0, 23.3; ketone tautomer (minor): 203.8, 158.4, 429.9, 129.6, 114.11, 70.3, 55.3, 33.5, 29.8.

4-Methoxybenzyl-3-oxobotanal (2)

2

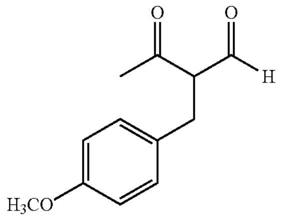

Synthesis sequence

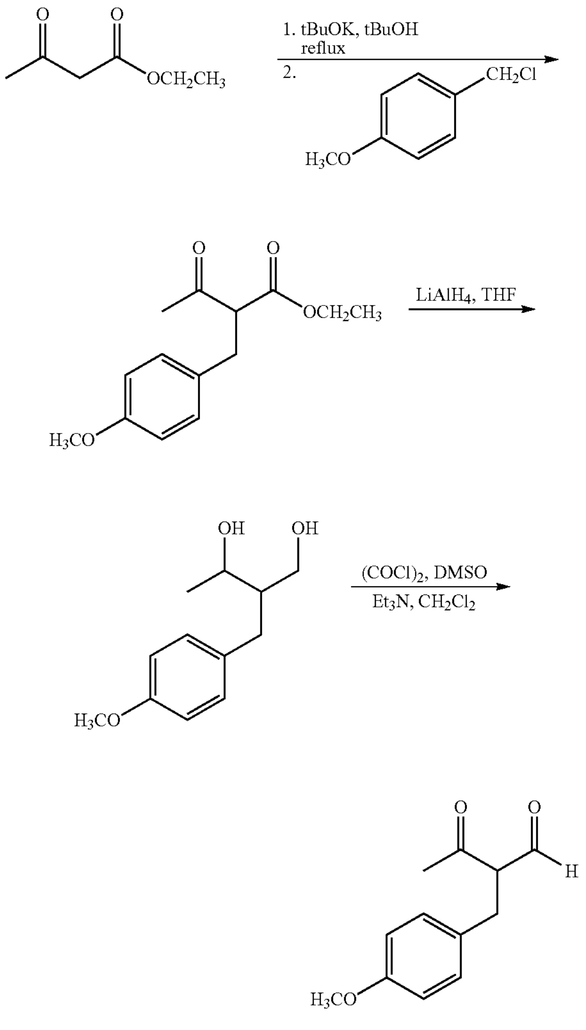

2

Procedures for Scheme

Ethyl 2-(4-methoxybenzyl)-3-oxobutanoate

Potassium tert-butoxide (1.121 g, 10 mmol) was dissolved in tert-butyl alcohol (25 mL) by refluxing for 25 min. The reaction mixture was cooled to room temperature and ethyl acetoacetate (1.206 g, 9.3 mmol) was added dropwise over 20 min. The reaction mixture was stirred for 20 min and then 4-methoxybenzyl chloride (1.457 g, 93 mmol) was added. The reaction mixture was stirred at 50° C. overnight. Water (20 mL) was added dropwise and the resulting mixture was extracted with ethyl acetate. Organic extracts were combined, dried over anhydrous magnesium sulfate, and concentrated under reduced pressure. The crude product was purified via column chromatography on silica gel to afford the desired product as a colorless (1.845 g, 79%).

The product was obtained as a 3:1 mixture of ketone and enol tautomers which is reflected in its NMR data: $^1$H NMR ($CDCl_3$, 300 MHz) δ ketone tautomer (major); 7.09 (d, J=8.4 Hz, 2H), 6.81 (d, J=8.7 Hz, 2H), 4.15 (q, J=7.5 Hz, 2H), 3.78 (s, 3H), 3.73 (t, J=7.4 Hz, 1H), 3.10 (d, J=7.8 Hz, 2H), 2.18 (s, 3H), 1.24 (t, J=7.5 Hz, 3H); enol tautomer (minor): 7.04 (d, J=8.4 Hz, 2H), 6.78 (d, J=8.7 Hz, 2H), 4.19 (q, J=7.5 Hz, 2H), 3.78 (s, 3H), 3.13 (s, 2H), 2.28 (s, 3H), 1.29 (t, J=7.5 Hz, 3H).

2-(4-Methoxybenzyl)-butane-1,3-diol

A solution of ethyl 2(4-methoxybenzyl)-3-oxobutanoate (3.311 g, 13.2 mmol) in anhydrous THF (26 ml) was cooled to 0° C. Lithium aluminum hydride (0.755 g, 19.8 mmol) was added in portions and the resulting reaction mixture was stirred at 0° C. for 30 min then allowed to warm up to room temperature. The reaction was quenched with 2M aq Rochelle salt solution (20 ml) and then extracted with ethyl acetate. Organic extracts were combined, washed with brine, dried over anhydrous $MgSO_4$, and concentrated under reduced pressure. The crude product was separate via column chromatography on silica gel to afford desired product as a colorless oil (1.27 g, 45%).

The product formed as a mixture of diastereomers, which made characterization by $^1$H NMR difficult. $^{13}$C NMR ($CDCl_3$, 75 MHz) δ 157.9, 132.22, 132.18, 130.0, 129.9, 113.88, 113.84, 71.2, 70.7, 65.9, 63.9, 63.2, 55.3, 47.9, 47.3, 34.1, 31.2, 22.2, 19.4.

4-Methoxybenzyl-3-oxobutanal (2)

Anhydrous dimethyl sulfoxide (1.50 g, 19.6 mmol) was dissolved in dry dichloromethane (50 mL) under Ar atmosphere and the resulting solution was cooled to −78° C. Oxalyl chloride (1.25 g, 9.9 mmol) was added dropwise and the reaction mixture was stirred for 30 min. A solution of 2-(4-methoxybenzyl)-butane-1,3-diol (1.03 g, 4.9 mmol) in dry dichloromethane (5 ml) was added dropwise and the resulting cloudy reaction mixture was stirred for 30 min. Triethyl amine (3.84 g, 38 mmol) was added dropwise. The reaction mixture was stirred at for −78° C. 5 min and then allowed to warm up to room temperature. Water (25 mL) was added to the reaction mixture and then the reaction mixture was extracted with diethyl ether. Organic extracts were combined and washed successively with 1M aq HCl, 5% aq $NaHCO_3$, and brine, then dried over anhydrous magnesium sulfate, and concentrated under reduced pressure. The crude product was purified via column chromatography on silica gel to afford the desired product 2 as a colorless oil (0.252 g, 25%). $^1$H NMR ($CDCl_3$, 300 MHz) δ 14.94 (d, J=7.8 Hz, 1H), 7.82 (d, J=8.1 Hz, 1H), 7.08 (d, J=8.4 Hz, 2H), 6.85 (d, J=8.7 Hz, 2H), 3.80 (s, 3H), 3.47 (d, 2H), 2.04 (s, 3H); $^{13}$C NMR ($CDCl_3$, 75 MHz) δ 198.0, 174.8, 158.2, 131.6, 128.9, 114.0, 112.1, 55.3, 33.0, 25.2.

2-(4-Methoxybenzyl)-2-methylmalonaldehyde (3)

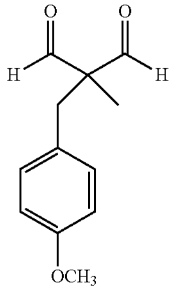

3

Synthesis sequence

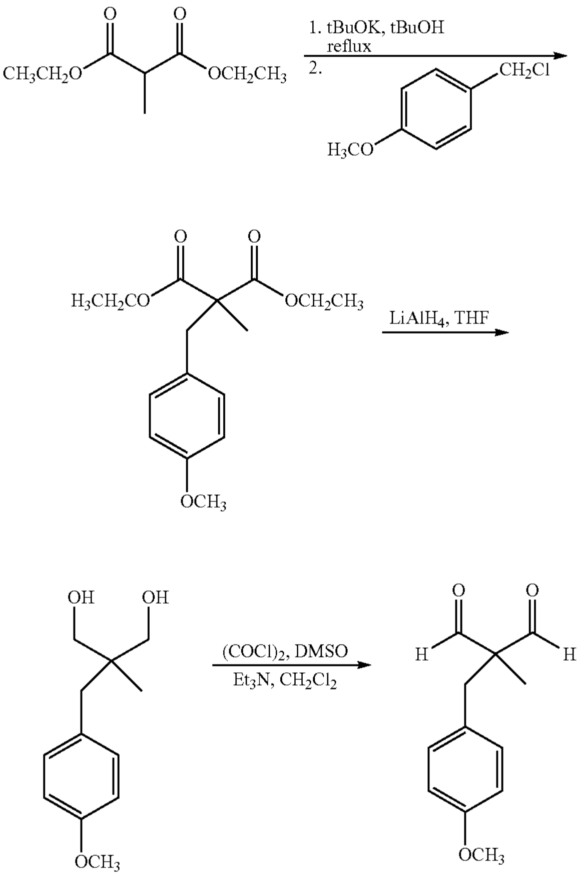

3

Procedures for Scheme

Diethyl 2-(4-methoxybenzyl)-2-methylmalonate

Potassium tert-butoxide (4.49 g, 40 mmol) was dissolved in tert-butyl alcohol (50 mL) by refluxing for 10 min. The reaction mixture was cooled to room temperature and diethyl methylmalonate (6.97 g, 40 mmol) was added dropwise over 20 min. The cloudy mixture was stirred for 20 min and then followed by 4-methoxybenzyl chloride (3.01 g, 19 mmol) was added dropwise. The reaction mixture was stirred at room temperature overnight. Water (25 mL) was added dropwise and the resulting mixture was extracted with ethyl acetate. Organic extracts were combined, dried over anhydrous magnesium sulfate, and concentrated under reduced pressure. The crude product was purified via column chromatography on silica gel to afford the desired product as a colorless oil (1.06 g, 21%). $^1$NMR ($CDCl_3$, 300 MHz) δ 7.04 (d, J=8.4 Hz, 2H), 6.80 (d, J=8.7 Hz, 2H), 4.19 (q, J=7.5 Hz, 4H), 3.78 (s, 3H), 3.16 (s, 2H), 1.32 (s, 3H), 1.26 (t, J=7.2 Hz, 6H); $^{13}$C NMR ($CDCl_3$, 75 MHz) δ 170.2, 158,5, 131.2, 128,2, 113.6, 61.3, 54.9, 40.2, 19.6, 14.1.

2-(4-Methoxybenzyl)-2-methylpropane-1,3-diol

A solution of diethyl 2-(4-methoxybenzyl)-2-methylmalonate (1.175 g, 4 mmol) anhydrous THF (10 ml) was cooled to 0° C. Lithium aluminum hydride (0.302 g, 8 mmol) was added in portions and the resulting reaction mixture was stirred at 0° C. for 30 min. The reaction was quenched with 2M aq Rochelle salt solution (20 ml) and then extracted with ethyl acetate. Organic extracts were combined, washed with brine, dried over anhydrous $MgSO_4$, and concentrated under reduced pressure. The crude product was separate via column chromatography on silica gel to afford desired product as a white solid (0.438 g, 52%). $^1$H NMR ($d_6$-DMSO, 300 MHz) δ 7.08 (d, J=8.4 Hz, 2H), 6.81 (d, J=8.4 Hz, 2H), 4.42 (t, J=5.55 Hz, 2H), 3.71 (s, 3H), 3.14 (d, J=5.4 Hz, 2H), 0.62 (s, 3H); $^{13}$C NMR ($d_6$-DMSO, 75 MHz) δ 157.8, 131.8, 130.8, 113.5, 65.5, 55.3, 40.9, 38.5, 19.0.

2-(4-Methoxybenzyl)-2-methylmalonaldehyde (3)

Anhydrous dimethyl sulfoxide (0.623 g, 8 mmol) was dissolved in dry dichloromethane (18 mL) wider Ar atmosphere and the resulting solution was cooled to −78° C. Oxalyl chloride (0.502 g, 4 mmol) was added dropwise and the reaction mixture was stirred for 30 min, A solution of 2-(4-methoxybenzyl)-2-methylpropane-1,3-diol (0.322 g, 1.77 mmol) in dry dichloromethane (9 ml) was added dropwise and the resulting cloudy reaction mixture was stirred for 30 min. Triethyl amine (1.569 g, 15.5 mmol) was added dropwise. The reaction mixture was stirred at for −78° C. 5 min and then allowed to warm up to room temperature. Water (25 mL) was added to the reaction mixture and then the reaction mixture was extracted with diethyl ether. Organic extracts were combined and washed successively with 1M aq HCl, 5% aq $NaHCO_3$, and brine, then dried over anhydrous magnesium sulfate, and concentrated under reduced pressure. The crude product was purified via column chromatography on silica gel to afford the desired product 3 as a colorless oil (0.133 g, 36%). $^1$H NMR ($CDCl_3$, 300 MHz) δ 9.71 (s, 2H), 7.02 (d, J=8.4 Hz, 2H), 6.82 (d, J=8.4 Hz, 2H), 3.78 (s, 3H), 2.20 (d, 3H), 2.07 (s, 2H); $^{13}$C NMR ($CDCl_3$, 75 MHz) δ 198.0, 174.8, 158.2, 131.6, 128.9, 114.0, 112.1, 55.3, 33.0, 25.2.

II. Reactions of Model Reactive Heads 1 and 2 with N-ethylurea

The model reactive heads react with citrulline according to create the following structure (as also schematically illustrated in FIG. 10):

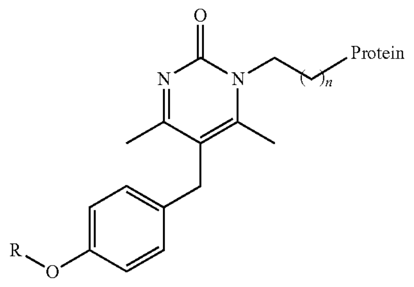

The reactive heads synthesized above were reacted with N-Ethylurea, which closely simulates the chemical structure of citrulline, to demonstrate the reactivity of the reactive heads with citrulline:

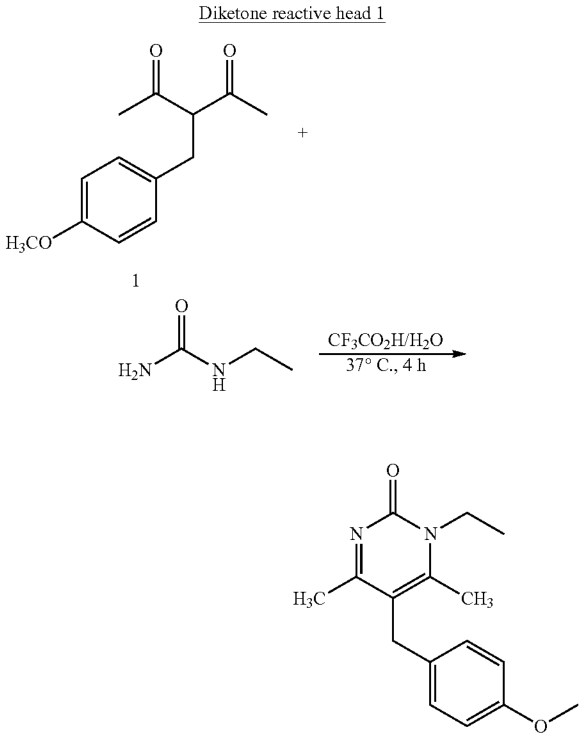

1

N-Ethylurea (45 mg, 0.5 mmol) and 3-(4-methoxybenzyl) pentane-2,4-dione (1) (550 mg, 2.5 mmol) were dissolved in a 1:1 mixture of water and trifluoroacetic acid (2 mL) and the resulting mixture was heated at 37° C. for 4 hours. Water (4 ml) was added and the resulting mixture was extracted with dichloromethane. Organic extracts were combined, washed with water, dried over anhydrous magnesium sulfate, and concentrated under reduced pressure to afford 0.352 g of the crude product. Cyclization product was identified by comparison of the $^1$H NMR spectrum with the $^1$H NMR of the 1-ethyl-4,6-dimethylpyridin-2(1H)-one that was previously synthesized by us. $^1$H NMR analysis showed an about 1:5 ratio of the cyclization product and the starting probe 1, indicating that N-ethylurea reacted almost quantitatively. $^1$H NMR ($CDCl_3$, 300 MHz) δ 6.98 (d, J=8.7 Hz, 2H), 6.80 (d, J=8.7 Hz, 2H), 4.24 (q, J=7.5 Hz, 2H), 3.80 (s, 3H), 2.61 (s, 3H), 2.62 (s, 3H), 1.39 (t, J=7.1 Hz, 3H).

Ketoaldehyde reactive head 2

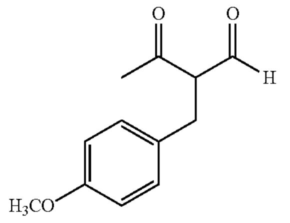

2

+

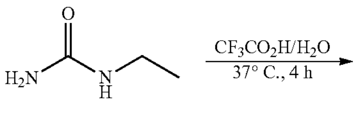

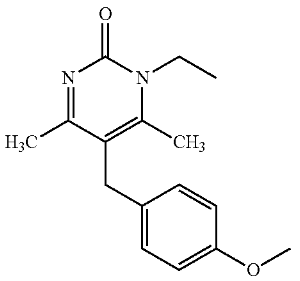

or/and

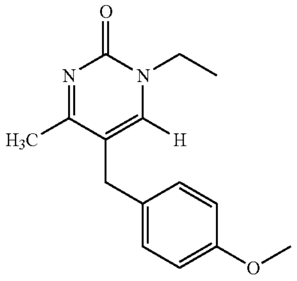

N-Ethylurea (46 mg, 0.5 mmol) and 4-methoxybenzyl-3-oxobutanal (2) (141 mg, 0.68 mmol) were dissolved in a 1:1 mixture of water and trifluoroacetic acid (2 mL) and the resulting mixture was heated at 37° C. for 4 hours. Water (4 ml) was added and the resulting mixture was extracted with dichloromethane. Organic extracts were combined, washed with water, dried over anhydrous magnesium sulfate, and concentrated under reduced pressure to afford 0.121 g of the crude product. $^1H$ NMR analysis showed an almost complete consumption of reactive head 2. The crude product was then separated via column chromatography on silica gel to afford the cyclization product (68 mg, 53% yield). $^1H$ NMR ($CDCl_3$, 300 MHz) δ 8.35 (s, 1H), 7.02 (d, J=8.7 Hz, 2H), 6.85 (d, J=8.7 Hz, 2H), 4.12 (q, J=7.5 Hz, 2H), 3.79 (s, 3H), 3.75 (s, 2H), 2.31 (s, 3H), 1.34 (t, J=7.1 Hz, 3H).

However, all of the model reactive head compounds lacked any inherent functionality for the attachment of the detection tag, e.g., a probe linker forming the detection tag with a read-out tag attached to the probe linker opposite the reactive head. To address this lack of functionality, a carbon-carbon triple bond (alkyne) is attached to the benzene ring via an $OCH_2$ reactive head linker. Here are the structures for all three reactive heads including the C≡C bond:

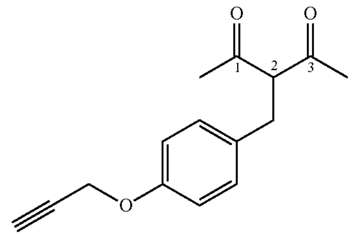

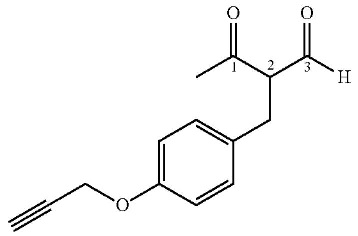

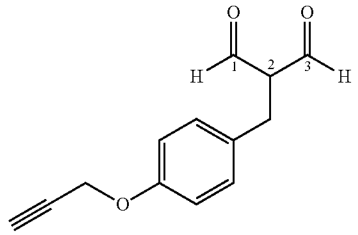

Figure 2:
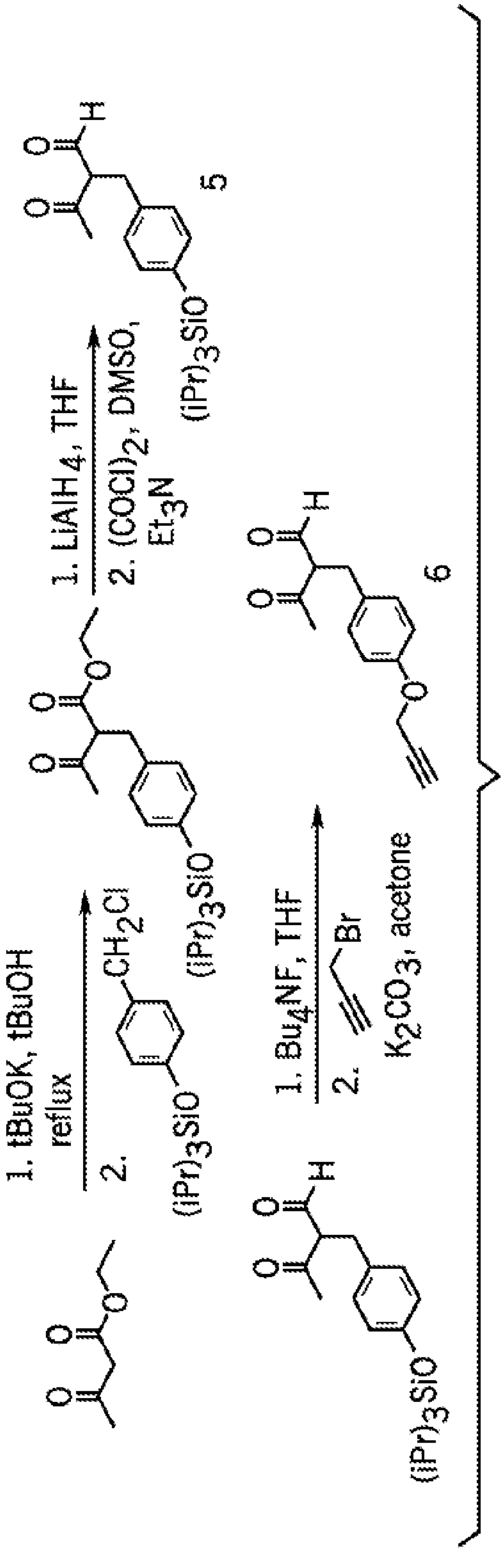
FIG. 2 is a scheme for the synthesis of a ketoaldehyde-based reactive head according to one exemplary embodiment of the invention.

The synthesis scheme as illustrated in FIG. 2 for the reactive head for the probe begins with alkylation of ethyl acetoacetate with an appropriate benzyl chloride, in this particular case a protected p-hydroxybenzyl chloride 4. We have already demonstrated that this chloride can be efficiently prepared from commercially-available starting materials in three steps as shown in the exemplary scheme of FIG. 1.

After a large-scale synthesis of this benzyl chloride using the exemplary scheme of FIG. 1, the benzyl chloride will then be reacted with ethyl acetoacetate using previously optimized reaction conditions as listed in FIG. 2. Complete reduction of both ester and ketone to alcohol followed by Swern oxidation will generate the desired ketoaldehyde moiety 5. Removal of the triisopropylsilyl protecting group followed by alkylation of the phenol with propargyl bromide will complete the synthesis of the desired reactive head 6.

Figure 3:
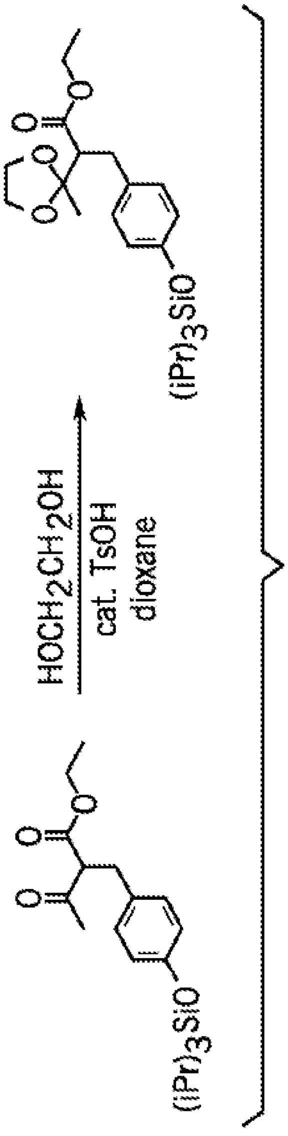
FIG. 3 is a scheme or the synthesis of a ketoaldehyde-based reactive head according to another exemplary embodiment of the invention.

In the scheme of FIG. 2, the oxidation of the diol is the only low yielding step, though the yield is sufficient to generate a desired amount of the reactive head for further testing. The yield might be improved by changing the order of the steps with deprotection/alkylation being done prior to the Swern oxidation step. Another alternative would involve protection of a ketone functional group as an acetal, as shown in the scheme of FIG. 3, so that only an ester functional group is subjected to reduction/oxidation sequence.

Thus, the parts of primary importance to the structure of the above variations of the reactive heads are 1) the 1,3-dicarbonyl structure which is reactive with citrulline; and 2)

the triple bond which is reactive with the detection tag, and optionally the linker structure of the detection tag. The structure between the reactive head and the triple bond can be varied depending on the ease and convenience of synthesis of the reactive tag structure and this can be readily varied.

As follows are sonic alternative variations of the structure located between the reactive head and the C—C triple bond (shown only for ketone-ketone reactive head, but applicable to ketone-aldehyde and aldehyde-aldehyde structures as well), or other reactive head linker structure, which may be employed individually or in combination with one another:

1) Variations in the location of the —OR substituent on the benzene ring:

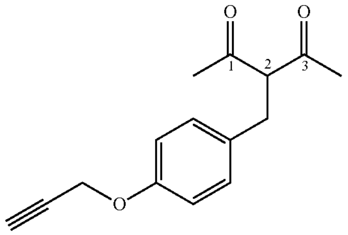

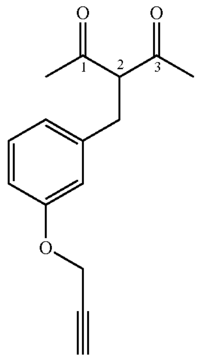

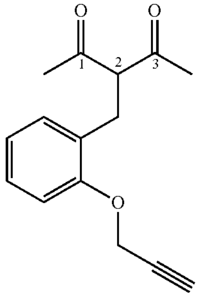
;

2) Variations in the functional group present in the linker attaching the triple bond to the benzene ring. Illustrated below in an exemplary embodiment is a nitrogen in place of an oxygen, but the substituent can also be a carbon, or other suitable linking atom, and the number of carbons in the chain can be varied. This substituent also can be attached in the different place on the benzene ring. In the below structure, R can be any alkyl group, or an oxygen-containing function group, including, but not limited to a C═O-alkyl group or (C═O)—O-alkyl group, or a PEG-based linker —$(OCH_2CH_2)_n$, where n=2 to 12:

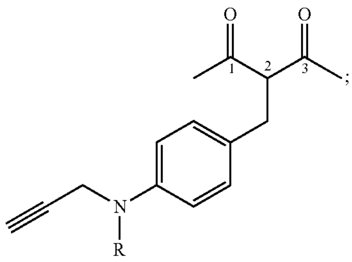
;

3) Variations where a second ring is introduced, where the second ring can vary in size between 5 to 10 carbon atoms and can include an oxygen or a nitrogen substitution in the ring of the type described in variation 2). Introduction of the ring can make the overall synthesis of the reactive head easier because there are easily accessible bicyclic molecules that can be converted into the desired structure in two to three steps. Also, modifications of the substituent with the triple bond described in variations 1) and 2) can be made here as well.

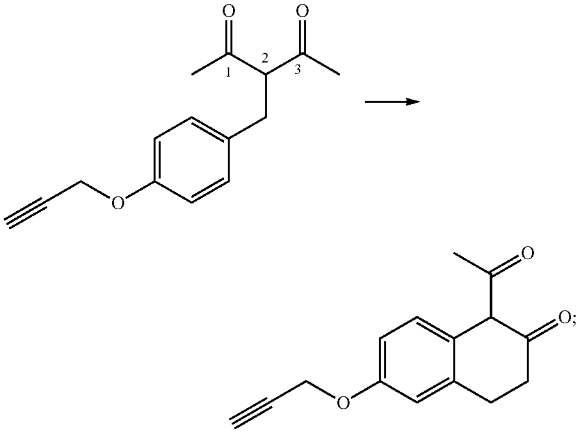
;

4) Another alternative to the structure of the reactive head is a change regarding the point of attachment of the benzene ring. In the initial reactive head structures, it is attached to the carbon at position 2 (indicated above in variation 3), but it can also be attached to either ketone group, either directly or through an alkyl chain reactive head linker of up to 10 carbons, and isomers thereof with any location for the attachment of to the benzene ring.

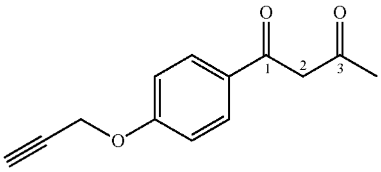

-continued

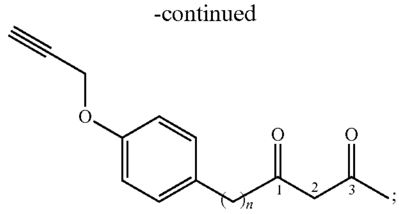

;

5) The same can be done for the ketone-aldehyde reactive head as illustrated in the exemplary embodiment below with similar linking groups to variation 4) above, and isomers thereof with regard to the point of attachment to the benzene ring.

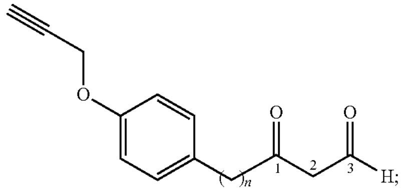

6) Further, all the previously disclosed modifications of the benzene ring and the triple bond substituent listed above for the reactive head structures can be done for these molecules, and isomers thereof, as well. Exemplary ketone-aldehyde structures with the additional second ring are shown below:

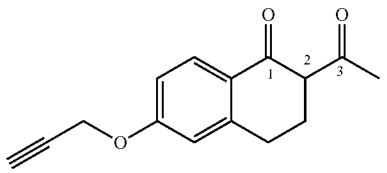

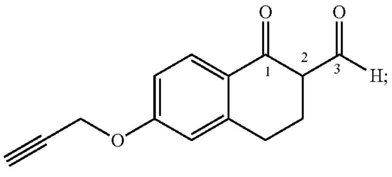

and

7) Finally, in the ketone group(s) of the ketone-ketone and ketone-aldehyde reactive head structures in place of the $CH_3$ group(s) shown, other alkyl substituents with chain lengths up to four carbons can be substituted, including but not limited to ethane, propane, and, butane, among others. Further substituents can include a benzene ring, as also illustrated below. Of particular interest are the derivatives containing a trihalomethyl group, such as a trifluoromethyl group $CF_3$ (shown below) to enhance the reactivity of the probes.

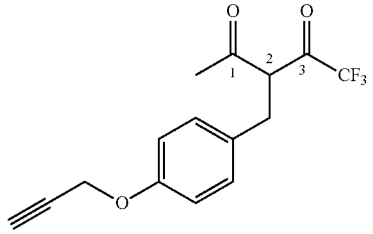

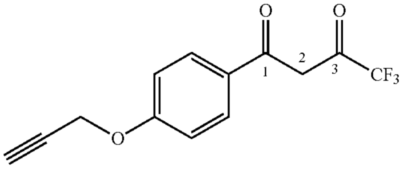

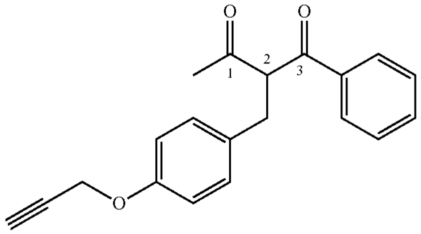

.

As stated previously, it is also within the scope of the present disclosure that these variations can be combined with one another, such that multiple variations can be utilized within individual reactive head structures.

B.) Synthesis of Detection Tags

Figure 10:
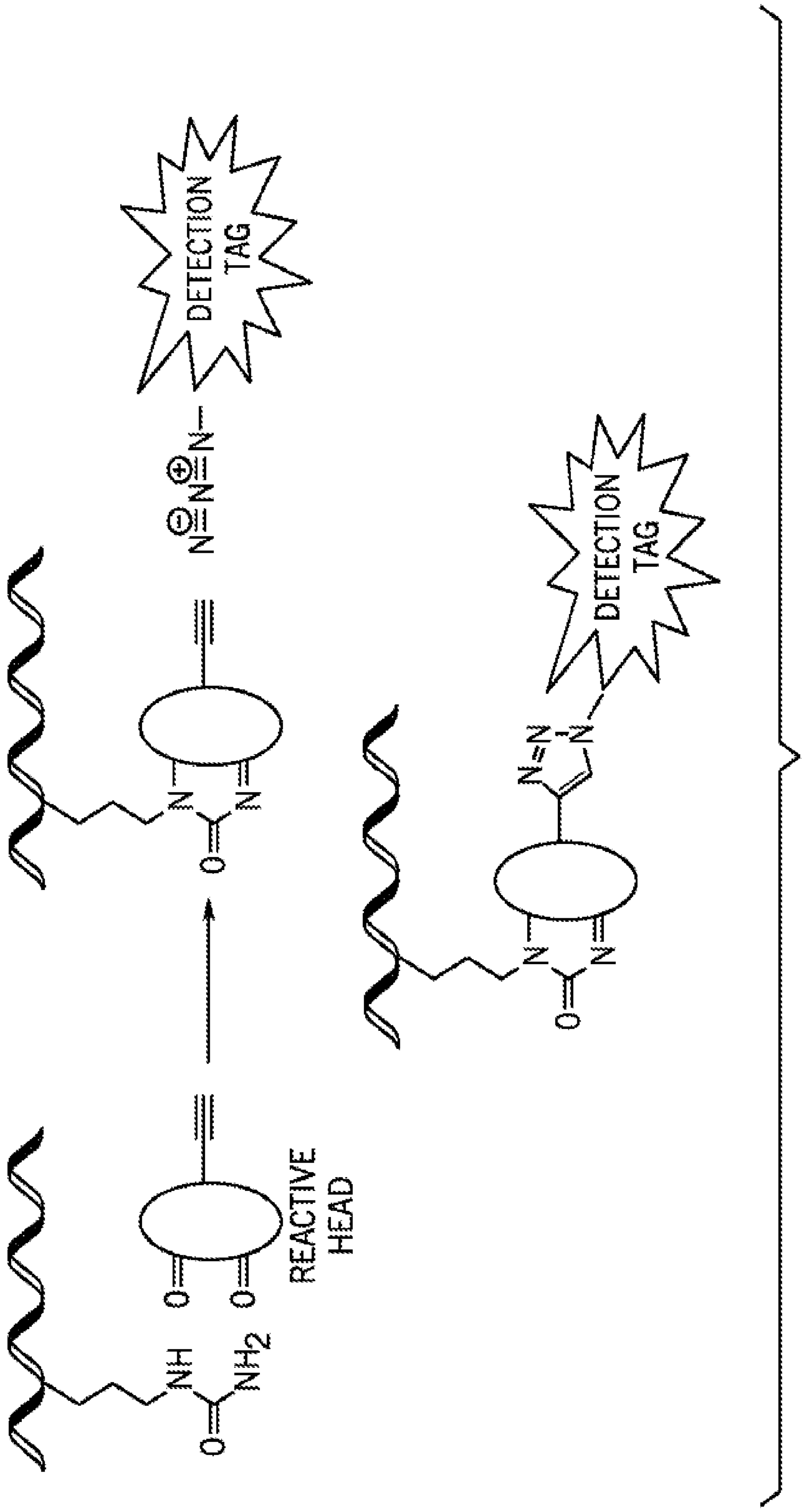
FIG. 10 is a schematic view of an exemplary method of use of the reactive head and detection tag in a modular detection process according to the present disclosure.

Separate from the synthesis of the reactive heads, multiple types of linker and read-out or detection tag structures can be synthesized for later connection to the reactive head that has reacted with citrulline in order to enable the citrulline to be identified by the method(s) defined by the read-out or detection tags. In one example of the use of the probes, as schematically illustrated in FIG. 10, a reactive head(s) can be utilized to label the citrulline present in a sample. As only the reactive head is used to bond with the citrulline, the small size of the reactive head provides more efficient labeling of the citrulline that is present than the prior art probes which include the linker and detection tag when bonding with the citrulline Once the reactive head(s) are bonded to the citrulline, the linker including the selected detection tag can be introduced and bonded to the reactive head in order to enable the citrulline to be detected using the method associated with the detection tag. Further, the sample can be split to allow different portions of the sample to use different detection tags and thus different detection methods in order to provide orthogonal read outs of the sample.

This results in a large number of probe structures with the large number of different reactive head structures that can be later connected to and utilized with different detection tags and linker structures. The detection tags that can be used with the linker to be connected to the reactive head include fluorophores, mass-spec tags, antigens, nanoparticles, quantum dots, and microbeads, among others. Some examples of the detection tags that can be utilized with the reactive heads disclosed above and have been synthesized will now be described.

1. Formation of Fluorescent Tag

7-Substituted 3-coumarincarboxylic acids are widely used as fluorophore probes and are easy to synthesize.

Figure 4:
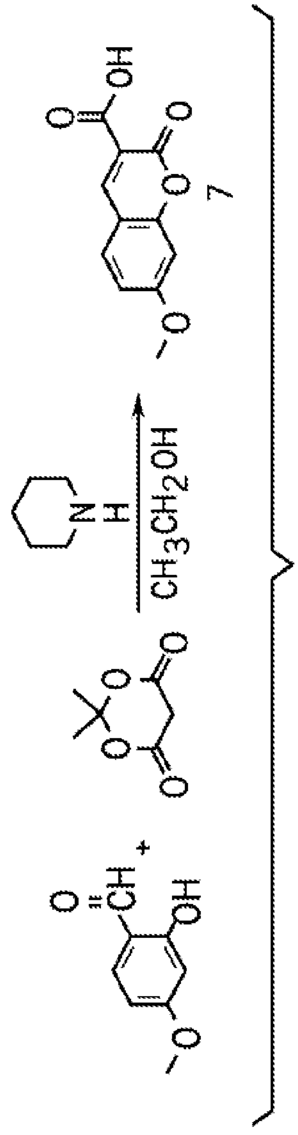
FIG. 4 is a scheme for the synthesis of 7-methoxycoumarin-3-carboxylic acid according to the present disclosure.
Figure 5:
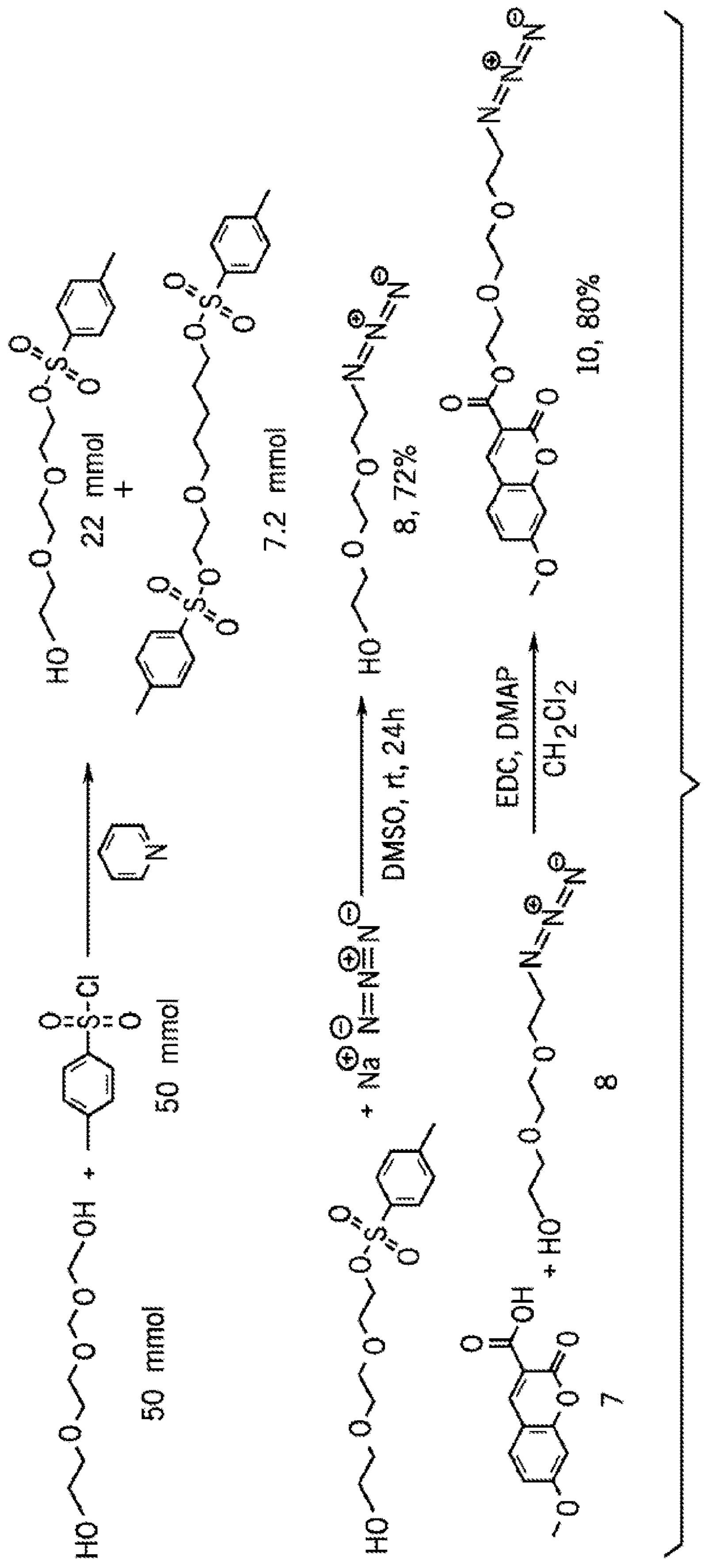
FIG. 5 is a scheme for the synthesis of a fluorophore probe according to the present disclosure.

7-methoxycoumarin-3-carboxylic acid 7 and 7-diethylaminocoumarin-3-carboxylic acid have been successfully synthesized by using the reaction scheme of FIG. 4. Synthesis of fluorescent detection tags was completed by attachment of an azide-modified linker. The required linker 8 has been synthesized by us on a large scale in two straightforward steps and then attached it to 7-methoxycoumarin-3-carboxylic acid to generate an azide-modified fluorescent tag 10 2-(2-(2-azidoethoxy)ethoxy)ethyl 7-methoxycoumarin-3-carboxylate in 80% yield, using the exemplary scheme of FIG. 5.

10

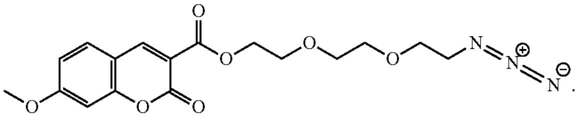

An additional coumarin that can be used is 2-(2-(2-azidoethoxy)ethoxy)ethyl 7-(diethyamino)-2-oxo-2H-chromene-3-carboxylate or 2-(2(2-azidoethoxy)ethoxy) ethyl 7-(diethylamino)coumarin-3-carboxylate which has the following structure:

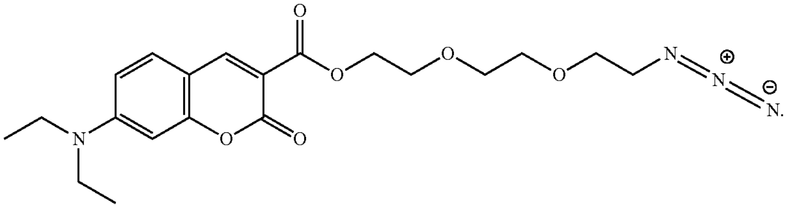

horseradish-peroxidase conjugated streptavidin. Only proteins modified with the biotinylated-tags will be detected.

With these biotinylated tags it is possible to isolate and identify citrullinated proteins from complex biological tissues by utilizing biotin/streptavidin affinity bead methods. Using skinned myocytes from porcine heart, a tissue that is a ready source of myofilament proteins that are easily citrullinated, the myofilaments will be treated with PAD4 to generate citrullinated arginines. Proteins will be reacted with the biotinylated-tag, and tagged proteins will be isolated using streptavidin-agarose beads. Tagged, citrullinated proteins will be eluted from the streptavidin column using excess biotin and heat. In the fully mature proteomics workflow, mass spectrometric analysis is performed to identify citrullinated proteins and their citrullination sites.

Figure 6:
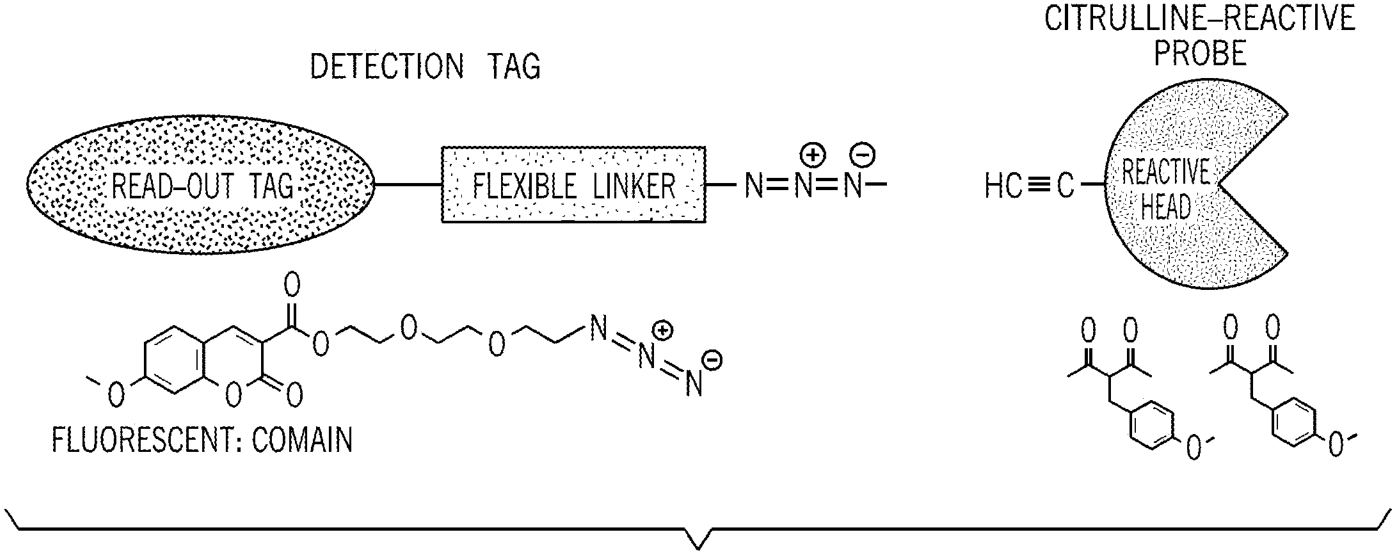
FIG. 6 is a schematic representation of the detection of citrullinated peptides and proteins by a fluorophore probe of FIG. 5.
Figure 7:
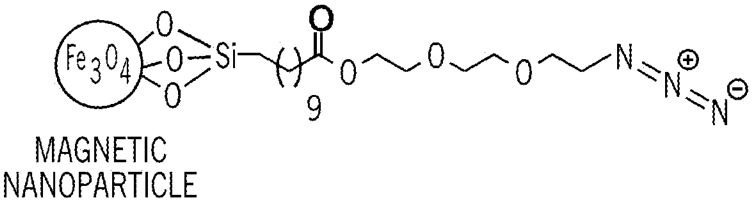
FIG. 7 is a representation of the structure of a detection bead based on superparamagnetic nanoparticles.

3. Formation of Nanoparticle-based Tags for Magnetic Capture of Citrullinated Proteins While fluorescent 10 and biotinylated 11 tags are ideal for detection of citrullinated peptides and proteins, as schematically shown in FIG. 6, and capture of biotinylated proteins using streptavidin beads has been in use for several decades, unfortunately displacement of the protein from the beads often requires harsh conditions. As a result, the development of additional detection tags that allow for isolation of the labeled proteins and peptides will greatly expand the utility and commercial appeal of the present method. We propose to develop a detection bead based on superparamagnetic nanoparticles as illustrated in FIG. 7.

Reaction conditions for attachment of the detection tags with the reaction head using a model compound phenyl propargyl ether, particularly solvent and concentration of the catalyst, were optimized, as discussed previously.

2. Formation of Biotinylated Tag

The linker 8 can additionally be attached to the carboxylic acid functional group of biotin, thus creating a read-out tag 11 that would be detected using its antibody protein streptavidin.

Superparamagnetic particles offer several advantages over other micronized beads.[13] They appear to have no magnetization in the absence of an external magnetic field, but are quickly magnetized once the field is applied. The superparamagnetic nanoparticles can be separated from the samples by the action of an external magnet. Most superparamagnetic nanoparticles are based on magnetite iron oxide $Fe_3O_4$ because these nanoparticles can be readily synthesized in a manner allowing the control of their size, and their surface can be modified by covalent attachment of silicon-based moieties.[13,14]

11

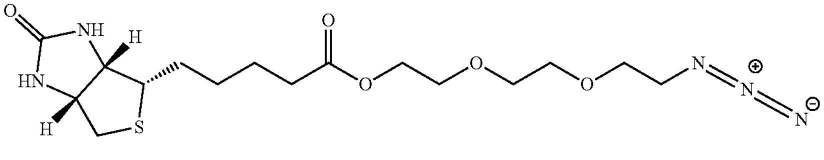

Figure 8:
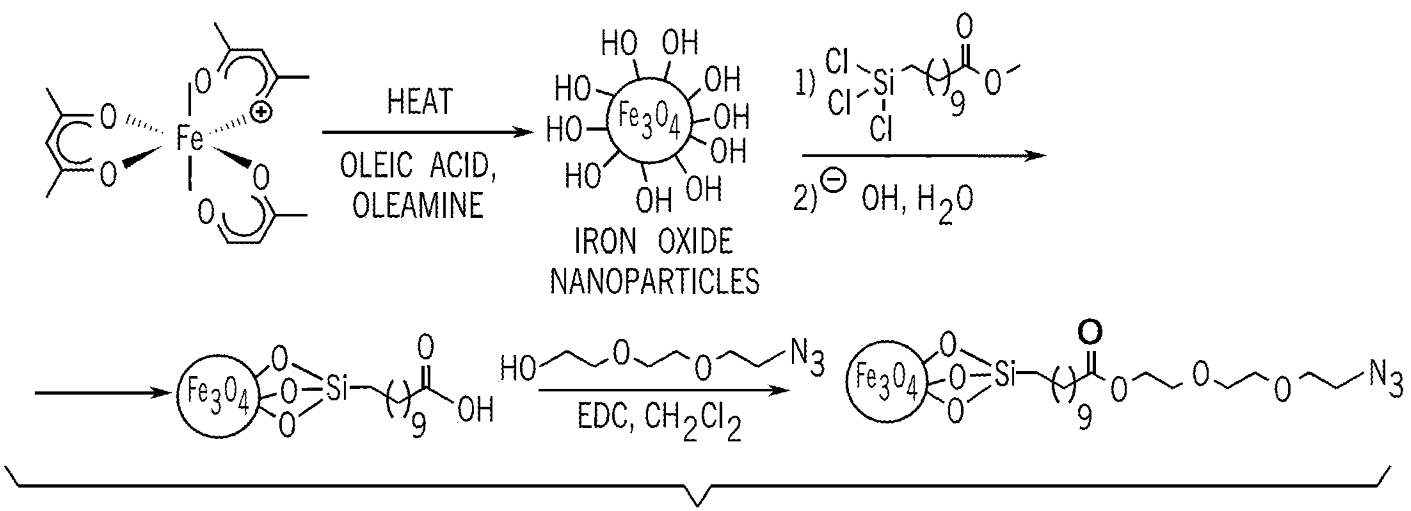
FIG. 8 is a scheme for the synthesis of the detection bead based on superparamagnetic nanoparticles of FIG. 7.

Fibrinogen is an oligomer comprised of three chains that are 63, 56 and 47 kDa, and is readily citrullinated by protein arginine deiminase 4 (PAD4). Isolated fibrinogen will be treated with PAD4 to generate citrullinated sites, then the citrullinated protein will be tagged using the biotinylated-CRP. The reaction's contents will be run out on an SDS-PAGE gel, which separates the protein subunits by their mass. The protein bands on the gel will be transferred to nitrocellulose, and biotin detection will be achieved using An initial approach to the synthesis and functionalization of the iron oxide nanoparticles is outlined in FIG. 8. First, nanoparticles themselves are prepared following literature procedures by thermal or microwave induced decomposition of iron complexes, such as iron(III) acetylacetonate in the presence of oleic acid and oleamine to prevent coagulation of nanoparticles.[14] The surface of the nanoparticles will then be functionalized to introduce an azide functional group necessary for the capture of the labeled citrulline. To achieve that we will first take advantage of the hydroxy groups on the surface of iron oxide nanoparticles which react readily with trichloro- or trimethyoxysilyl groups. Thus, a commercially available trichlorosilane bearing an ester functional group at the end of the alkyl chain would react with the hydroxyl groups on the surface of the nanoparticles to generate a surface modified nanoparticle as shown in the scheme of FIG. 8 The ester is then hydrolyzed to generate the carboxylic acid necessary for the attachment of the azide-modified linker using the reaction methodology developed previously to synthesize other detection tags.

Figure 9:
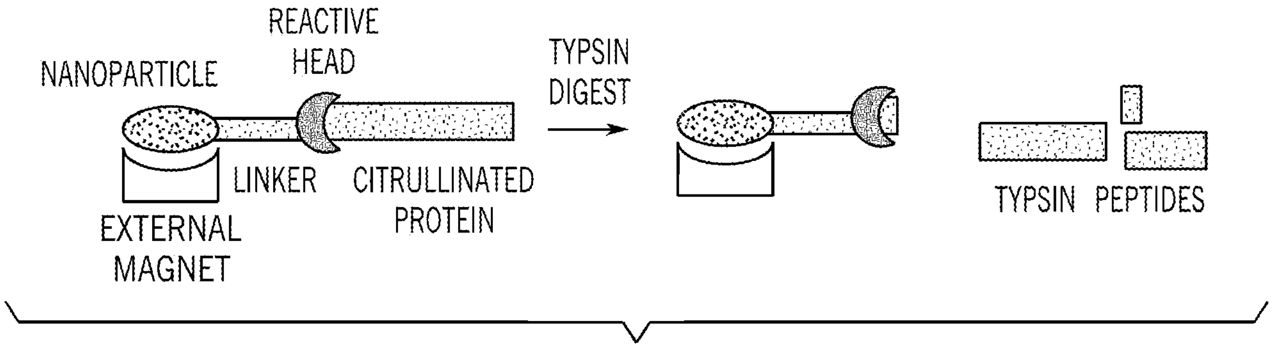
FIG. 9 is a schematic representation of the isolation, digestion and identification of trypsin peptides by mass-spectrometry using the detection bead based on superparamagnetic nanoparticles of FIG. 7.

After reaction of the CRP with citrullinated proteins prepared from skinned myocytes, derivatized citrullinated proteins will be isolated using a magnet applied externally to the reaction vessel. On-nanoparticle trypsin-digestion of proteins will release peptides, which will then be harvested and analyzed. Ultimately these peptides can be identified by mass-spectrometry as schematically illustrated in FIG. 9.

REFERENCES

The following references are expressly incorporated by reference herein in their entirety for all purposes.

1. Gudmann, N. S.; Hansen, N. U.; Jensen, A. C., Karsdalm, M. A., Siebuhr A. S. Biological relevance of citrullinations: diagnostic, prognostic and therapeutic options. Autoimmunity. 2015, 48, 73-79.
2. Fert-Bober, J.; Darrah, E.; Andrade F. Insights into the study and origin of the citrullinome in rheumatoid arthritis. Immunol Rev. 2019 Epub ahead of print https://onlinelibrary.wiley.com/doi/abs/10.1111/imr.12834
3. Larsen, D. N., et al. Citrullinome of *Porphyromonas gingivalis* Outer Membrane Vesicles: Confident Identification of Citrullinated Peptides. Mol Cell Proteomics. 2019, 19 (1) 167-180.
4. Jang, B. et al., Myelin Basic Protein Citrullination, a Hallmark of Central Nervous System Demyelination, Assessed by Novel Monoclonal Antibodies in Prion Diseases. Mol Neurobiol. 2018, 55, 3172-3184.
5. Ishigami, A. et al., Mass spectrometric identification of citrullination sites and immunohistochemical detection of citrullinated glial fibrillary protein in Alzheimer's disease. J Neurosci Res. 2015, 93, 1664-74.
6. Lazarus, R. C. et al. Protein Citrullination: A Proposed Mechanism for Pathology in Traumatic Brain Injury. Front Neurol. 2015, 6, 204. https://www.ncbi.nlm.nih-.gov/pmc/articles/PMC4585288/
7. Vanheule, V. et al. Cytokine. How post-translational modifications influence the biological activity of chemokines. Cytokine. 2018, 109, 29-5.
8. Olson J. S.; Lubner, J. M.; Meyer, D. J.; Grant, J. E. Human Peptidyl Arginine Deiminases Types 2 and 4 Recognize Distinct Structure-Specific Citrullination Motifs. Comp. Biol. and Chem. 2017, 70, 107-115.
9. Grant, J. E.: Li, H. Identification of Citrullination Sites by Mass Spectrometry. In Protein Deimination in Human Health and Disease: Nicholas A. P. Ed.; Springer Science+Business Media: New York, 2014; 347-365.
10. Grant, J. E.; Hu, J.; Liu, T.; Jain, M. R.; Elkabes; S., Li, H. Post-Translational Modifications in the Rat Lumbar Spinal Cord in Experimental Autoimmune Encephalomyelitis. J. Proteome Res. 2007, 6, 2786-2791.
11. Liu, T.; Donahue, K. C.; Hu, J.; Kournellas, M. P.; Grant, J. E.; Li, H.; Elkabes, S. Identification of Differentially Expressed Proteins in Experimental Autoimmune Encephalomyelitis (EAE) by Proteomic Analysis of the Spinal Cord. J. Prot. Res. 2007, 6, 2565-2575.
12. Grant, J. E.; Li, H., editors. Analysis of PTMs and Proteolytic Processing in Neuroscience. Springer Science+Business. Media: New York, 2016; Volume 114. Book volume.
13. Wu, W.; He, Q.; Jiang, C., Magnetic Iron Oxide Nanoparticles: Synthesis and Surface Functionalization Strategies. Nanoscale Research Letters 2008, 3 (11), 397
14. Ilyas, S.; Ilyas, M.; Van Der Hoorn, R. A. L.; Mathur, S., Selective Conjugation of Proteins by Mining Active Proteomes through Click-Functionalized Magnetic Nanoparticles. ACS Nano 2013, 7 (11), 9655-9663
15. Lewallen; Bicker; et al., Chemical Proteomic Platform To Identify Citrullinated Proteins. ACS Chemical Biology. 2015, 10, 2520-2528.

Various other embodiments of the invention are contemplated as being within the scope of the filed claims particularly pointing out and distinctly claiming the subject matter regarded as the invention.

The invention claimed is:

1. A chemical probe for the detection of the amino acid citrulline comprising a reactive head, wherein the reactive head is formed of 1,3-dicarbonyl moiety, and wherein reactive head is selected from the group consisting of:

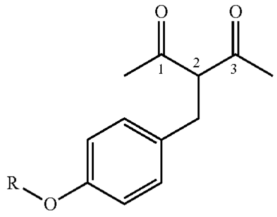

,

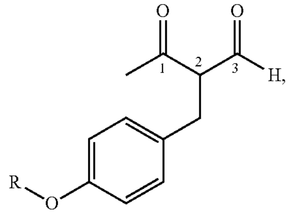

and

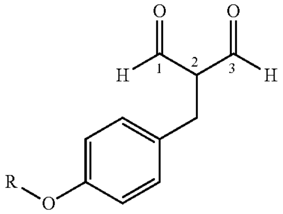

wherein R is selected from the group consisting of: an alkyne group, an alkene group, an alkyl group, or an oxygen-containing function group, including, but not limited to a C═O-alkyl group or (C═O)—O-alkyl group, and a PEG-based linker —$(OCH_2CH_2)_n$, where n=2 to 12.

2. A chemical probe for the detection of the amino acid citrulline comprising a reactive head, wherein the reactive head is formed of a 1,3-dicarbonyl moiety at one end of the reactive head, and wherein the reactive head includes a triple bond located at the other end of the reactive head opposite the 1, 3-dicarbonyl moeity.

3. The probe of claim 2 wherein the 1,3-dicarbonyl moiety includes a ketone-ketone, a ketone-aldehyde, or an aldehyde-aldehyde structure.

4. The probe of claim 3 wherein the reactive head has a structure selected from the group consisting of:

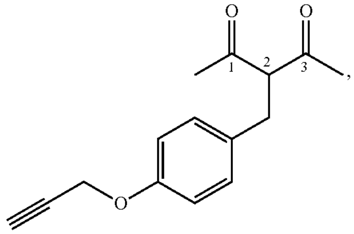

,

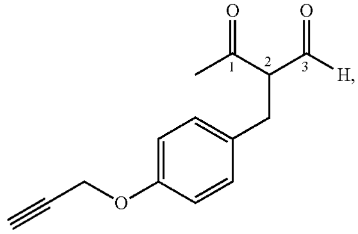

, and

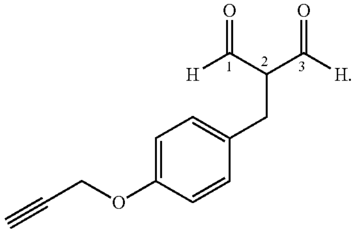

.

5. The probe of claim 3 wherein the reactive head has the structure:

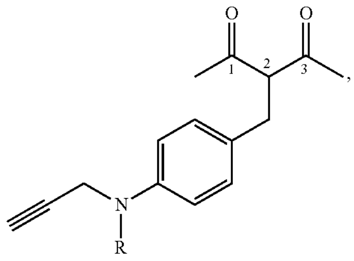

, wherein R is selected from the group consisting of: any alkyl group, or an oxygen-containing function group, including, but not limited to a C═O-alkyl group or (C═O)—O-alkyl group, and a PEG-based linker —$(OCH_2CH_2)_n$, where n=2 to 12.

6. The probe of claim 3 wherein the reactive head has the structure:

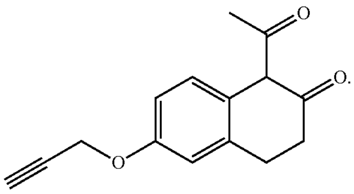 [SMILES: C#CCOc1ccc2c(c1)CCC(=O)C2C(C)=O]

.

7. The probe of claim 3 wherein the reactive head has the structure selected from the group consisting of:

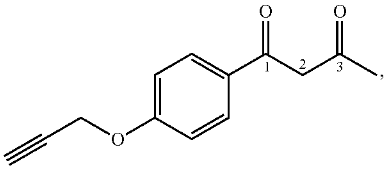

,

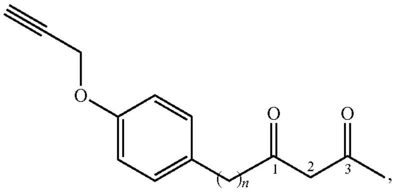

, and

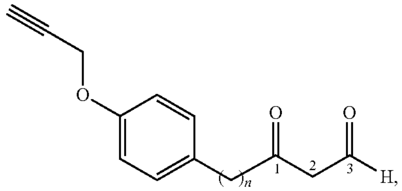

, wherein n=1 to 10.

8. The probe of claim 3 wherein the reactive head has a structure selected from the group consisting of:

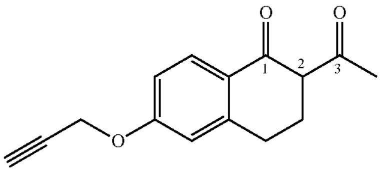

and

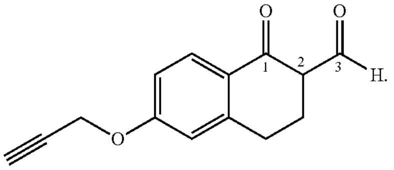

.

9. The probe of claim 3 wherein the reactive head has a structure selected from the group consisting of:

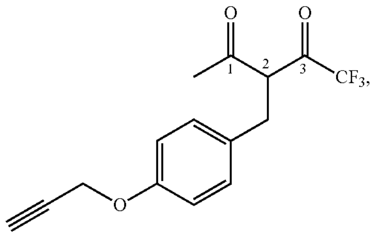

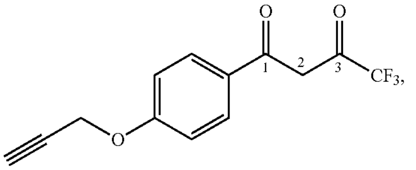 and

-continued

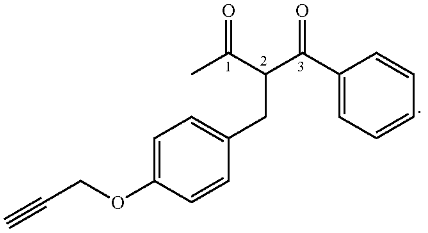

10. The probe of claim 1 or 2, further comprising a detection tag bonded to reactive head.

11. The probe of claim 10 wherein the detection tag comprises:

a. a probe linker attached to the reactive head; and b. a read-out tag attached to the probe linker.

12. The probe of claim 11 wherein the read-out tag is a fluorescent read-out tag.

13. The probe of claim 11 wherein the read-out tag is a biotinylated read-out tag.

14. The probe of claim 11 wherein the read-out tag is a superparamagnetic nanoparticle read-out tag.

15. The probe of claim 2, further comprising a detection tag bonded to reactive head, wherein the detection tag comprises:

a. a probe linker attached to the reactive head; and b. a read-out tag attached to the probe linker, and wherein the probe linker is an azide-modified probe linker.

16. The probe of claim 2, further comprising a detection tag bonded to the reactive head, wherein the detection tag comprises:

a. a probe linker attached to the reactive head; and b. a read-out tag attached to the probe linker, and wherein the read-out tag is a fluorescent read-out tag having the following formula:

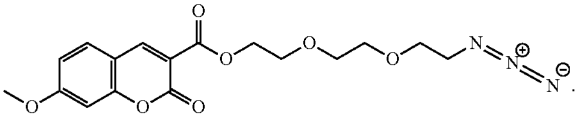 [SMILES: COc1ccc2cc(C(=O)OCCOCCOCCN=[N+]=[N-])c(=O)oc2c1]

17. The probe of claim 2, further comprising a detection tag bonded to the reactive head, wherein the detection tag comprises:

a. a probe linker attached to the reactive head; and b. a read-out tag attached to the probe linker, and wherein the read-out tag is a biotinylated read-out tag having the following formula:

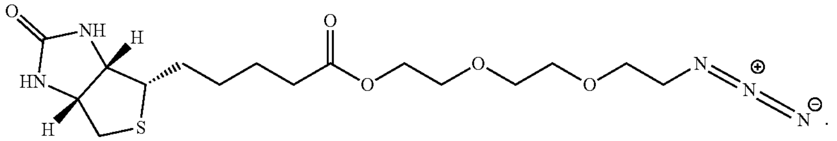 [SMILES: [N-]=[N+]=NCCOCCOCCOC(=O)CCCC[C@@H]1SC[C@@H]2NC(=O)N[C@@H]21]

18. The probe of claim 2, further comprising a detection tag bonded to the reactive head, wherein the detection tag comprises:

a. a probe linker attached to the reactive head; and b. a read-out tag attached to the probe linker, and wherein the read-out tag is a superparamagnetic nanoparticle read-out tag having the following formula:

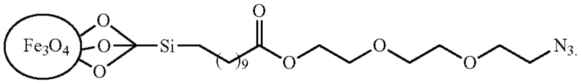

19. A method for detecting the presence of the amino acid citrulline in proteins from biological samples, the method comprising the steps of:

a) providing the detection probe of claim 1 or 2;

b) reacting the reactive head of the probe with citrulline to bond the probe to the citrulline;

c) bonding a detection tag to the reactive head; and d) detecting the detection tag of the probe bonded to the citrulline.

20. The method of claim 19, wherein the detection tag comprises:

a) a probe linker attached to the reactive head; and b) a read-out tag attached to the probe linker, and wherein the read-out tag is selected from the group consisting of: a fluorescent read-out tag, a biotinylated read-out tag, and a superparamagnetic nanoparticle read-out tag.

* * * * *